(12) United States Patent
Kim et al.

(10) Patent No.: US 10,053,489 B2
(45) Date of Patent: Aug. 21, 2018

(54) METHOD FOR PURIFYING ANTIBODY

(71) Applicant: Prestige Biopharma PTE. LTD., Singapore (SG)

(72) Inventors: Soo Kwang Kim, Daejeon (KR); Yong Ho Ahn, Daejeon (KR); Young Min Kim, Gyeonggi-do (KR); Dae Hae Song, Daejeon (KR)

(73) Assignee: Prestige Biopharma PTE, LTD (SG)

( * ) Notice: Subject to any disclaimer, the term of this patent is extended or adjusted under 35 U.S.C. 154(b) by 323 days.

(21) Appl. No.: 14/896,380

(22) PCT Filed: Jun. 3, 2014

(86) PCT No.: PCT/KR2014/004923
§ 371 (c)(1),
(2) Date: Dec. 5, 2015

(87) PCT Pub. No.: WO2014/196780
PCT Pub. Date: Dec. 11, 2014

(65) Prior Publication Data
US 2016/0122384 A1  May 5, 2016

(30) Foreign Application Priority Data
Jun. 5, 2013 (KR) ........................ 10-2013-0064803

(51) Int. Cl.
C07K 1/18 (2006.01)
C07K 16/06 (2006.01)
C07K 16/24 (2006.01)
C07K 16/22 (2006.01)

(52) U.S. Cl.
CPC .............. *C07K 1/18* (2013.01); *C07K 16/065* (2013.01); *C07K 16/22* (2013.01); *C07K 16/241* (2013.01)

(58) Field of Classification Search
None
See application file for complete search history.

(56) References Cited

U.S. PATENT DOCUMENTS 9,334,319 B2 * 5/2016 Ramasubramanyan ................. C07K 1/165
2006/0257972 A1 * 11/2006 Ishihara ............... C07K 16/065 435/69.1
2010/0135987 A1 * 6/2010 Hickman ............... C07K 16/00 424/130.1

FOREIGN PATENT DOCUMENTS

| WO | 2006/110277 A1 | 10/2006 |
| WO | 2007-108955 A1 | 9/2007 |
| WO | 2009-085765 A1 | 7/2009 |
| WO | 2010-048192 A2 | 4/2010 |
| WO | 2010127069 A1 | 11/2010 |

OTHER PUBLICATIONS

Fahrner et al. "Industrial Purification of Pharmaceutical Antibodies: Development, operation, and validation of chromatography processes." Biotechnology and Genetic Engineering Reviews, 18. (Year: 2001).*
Liu, Hui F., et al. "Recovery and Purification Process Development for Monoclonal Antibody Production," mAbs Landes Bioscience, Sep./Oct. 2010, vol. (2)5, pp. 480-499.
ISA/KR, International Search Report and Written Opinion for Int'l Appln No. PCT/KR2014/004923, dated Aug. 26, 2014, 10 pages.
"Extended European Search Report", European Patent Office, dated Dec. 23, 2016, 19808920.5.
Kelley, B.D. et al., "High_ Throughput Screening of Chromatographic Separations: IV. Ion-Exchange", Biotechnology and Bioengineering, Aug. 12008, vol. 100, No. 5, pp. 950-963.

* cited by examiner

*Primary Examiner* — Daniel E Kolker
*Assistant Examiner* — James L Rogers
(74) *Attorney, Agent, or Firm* — Umberg Zipser LLP

(57) ABSTRACT

The present invention relates to a method of purifying an antibody with high purity and high quality by removing impurities by sequential use of a cation-exchange column, a culture supernatant multilayer filter and an anion-exchange column without using a protein-A column that is an affinity chromatography column which is generally used for antibody purification.

14 Claims, 3 Drawing Sheets

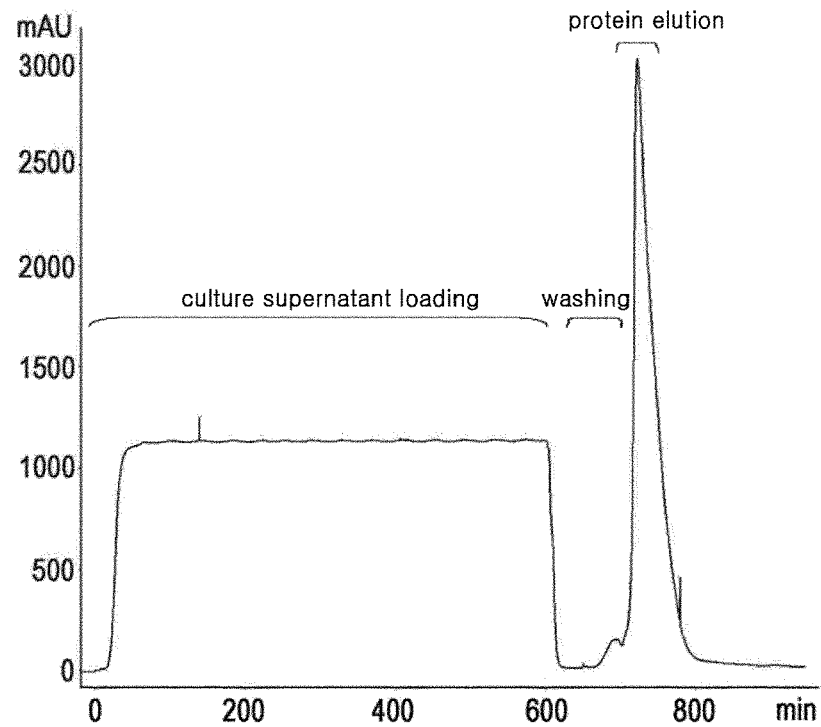
[Fig. 1]
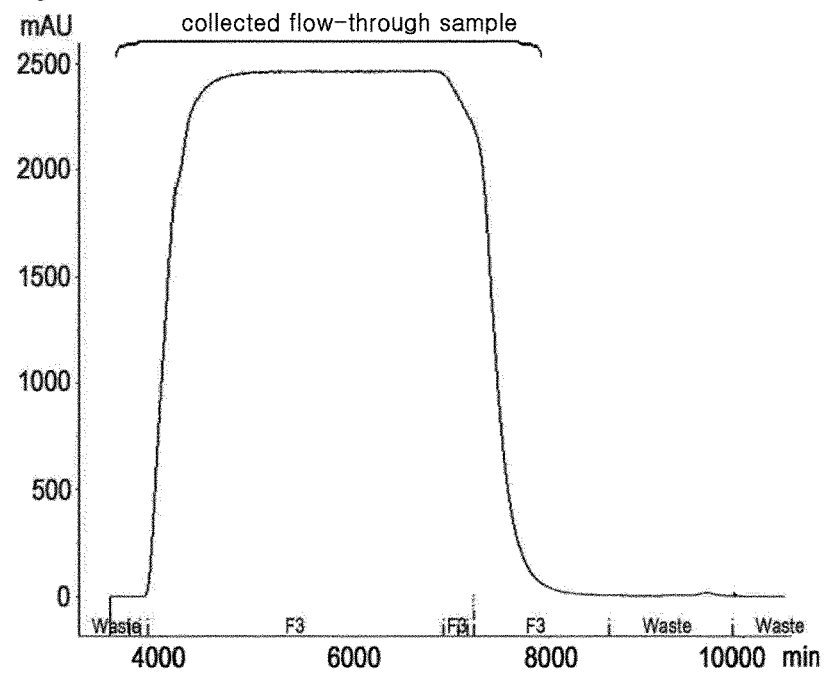
[Fig. 2]

[Fig. 3]
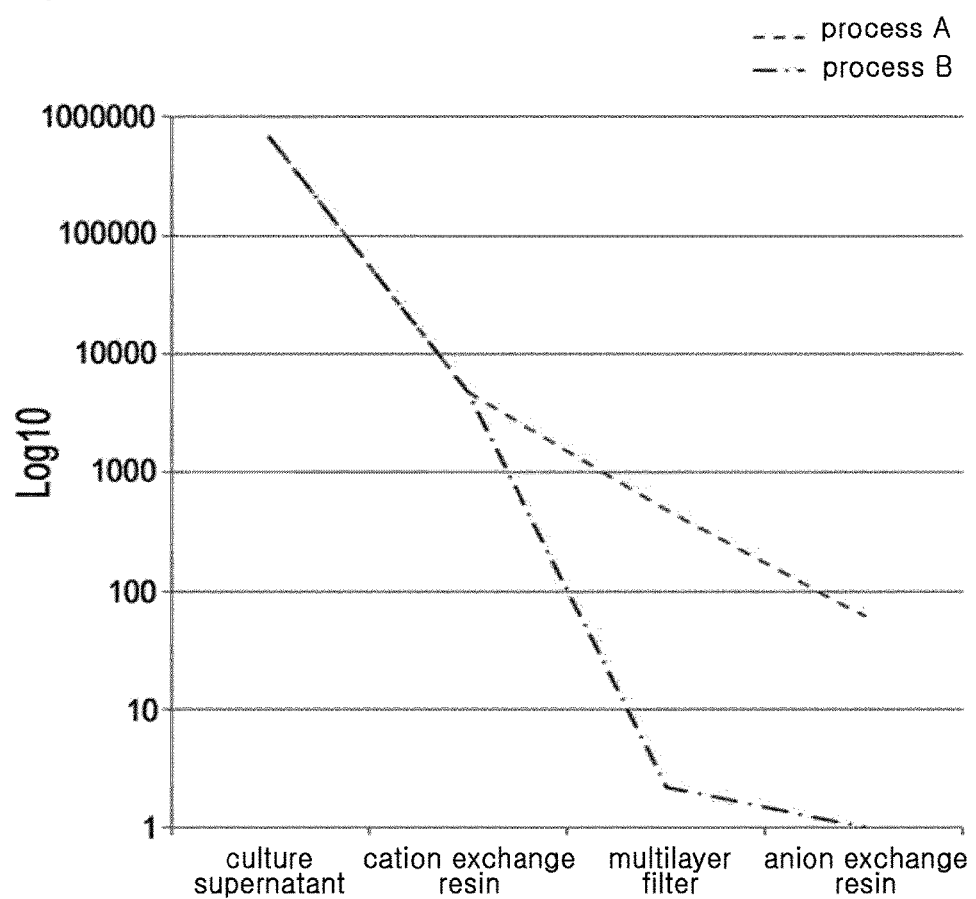

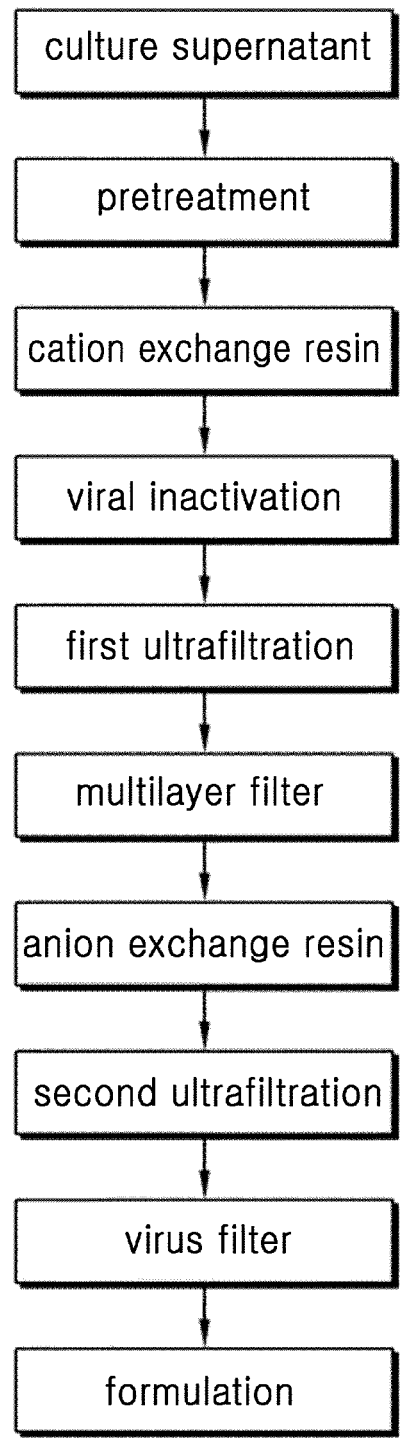
[Fig. 4]

METHOD FOR PURIFYING ANTIBODY

TECHNICAL FIELD

The present invention relates to a method of purifying an antibody with high purity and high quality by removing impurities by sequential use of a cation-exchange column, a multilayer filter and an anion-exchange column without using a protein-A column that is an affinity chromatography column, which is generally used for antibody purification.

BACKGROUND ART

Purification methods for monoclonal antibodies generally comprise the following four fundamental steps: (1) collection—separation of host cells from fermentation culture products; (2) capture—separation of antibodies from most components of purified collected materials; (3) fine purification—removal of remaining host cell contaminants and aggregates; and (4) formulation—placing antibodies in suitable carriers to ensure maximum stability and storage period of the antibodies. However, these steps do not always produce antibody compositions having sufficient purity for use in pharmaceutical circumstances. Thus, it is particularly important to have a method of producing and purifying a desired antibody having suitable purity for pharmaceutical use.

Protein-A chromatography makes it possible to substantially completely purify antibodies, particularly IgG, from cell culture supernatants by a single step, and thus is widely used in industrial antibody production. However, a protein-A chromatography column has a problem in that a ligand can leak somewhat from the column due to the repeated use of the column. This protein A or protein A fragment has affinity for IgG to form a complex with the antibody so as to contaminate the antibody and is also difficult to remove from a purified antibody. Particularly, because protein A is a bacterial protein, it can induce an undesired immune response, and thus should be removed from a purified antibody. Accordingly, processes of purifying antibodies using protein A chromatography have a problem in that it is required to monitor and remove the remaining protein A in each process.

However, large foreign pharmaceutical companies mostly use protein A chromatography for antibody purification, because protein A chromatography can achieve the high-purity purification of antibodies, even though it is expensive. However, due to the above-described problem, it is needed to develop a process capable of substituting for protein A chromatography. If a highly economic antibody purification process capable of substituting for protein A chromatography were developed, it could be very advantageous in cost terms because it could reduce the process cost by up to 50-70% compared to existing processes, and it could also prevent protein A contamination.

However, in the development of an antibody purification process that does not use a protein A chromatography column, it is important to develop a process that can show impurity removal efficiency comparable to that of a process that uses a protein A chromatography column. Particularly, antibody cultures produced using animal cells, particularly CHO cells, contain, in addition to a desired antibody, large amounts of impurities, such as host cell protein (HCP) and host cell DNA (HCD), derived from the CHO cells, and also contain cell growth factors. Thus, if an antibody is to be purified without using a protein A chromatography column, it is particularly important to determine the amount of impurities that can be removed in an initial stage. However, in order to develop an antibody purification process that can result in a low HCP level without using protein A chromatography, it is required to determine the kind and order of suitable chromatography processes and to develop procedures for optimization of processes, but it is difficult to achieve this determination and development.

DISCLOSURE OF INVENTION

Technical Problem

The present inventors have made extensive efforts to develop a method capable of purifying an antibody with high purity and high quality without using an expensive protein A chromatography column that is generally used for antibody purification, and as a result, have found that, when a cell-free culture supernatant having controlled pH and conductivity is purified sequentially by a cation-exchange column, a multilayer filter and an anion-exchange column, a high-quality antibody agent can be prepared by efficiently removing impurities such as host cell protein (HCP), thereby completing the present invention.

Solution to Problem

It is an object of the present invention to provide a method for purifying an antibody, the method comprising: (a) loading a sample, which comprises the antibody and at least one host cell protein (HCP) into an equilibrated cation-exchange column, washing the cation-exchange column, and then eluting the antibody bound to the column with elution buffer; (b) passing the eluate of step (a) through a multilayer filter, and collecting the filtrate; and (c) passing the filtrate of step (b) through an anion-exchange column, and collecting the flow-through.

Another object of the present invention is to provide an antibody purified by the above-described method.

Advantageous Effects of Invention

The use of the antibody purification method according to the present invention makes it possible to purify an antibody with high purity and high quality by effectively removing impurities such as host cell protein without using an expensive protein-A column.

BRIEF DESCRIPTION OF DRAWINGS

FIG. 1 shows a general elution profile in Fractogel™ EMD SO₃ chromatography which is included in both process B and process A of the present invention.

FIG. 2 shows conventional flow-through during loading and washing profiles in a Q Sepharose Fast Flow™ chromatography step which is included in both process B and process A of the present invention.

FIG. 3 is a graphic diagram showing the stepwise reduction of HCP in process B that uses a multilayer filter and process A that uses no multilayer filter.

FIG. 4 is a block diagram showing all the steps of a representative antibody purification method according to the present invention.

BEST MODE FOR CARRYING OUT THE INVENTION

The present invention provides a method for purifying an antibody, the method comprising: (a) loading a sample, which comprises the antibody and at least one host cell protein (HCP) into a cation-exchange column, washing the cation-exchange column, and then eluting the antibody bound to the column with elution buffer; (b) passing the eluate of step (a) through a multilayer filter, and collecting the filtrate; and (c) passing the filtrate of step (b) through an anion-exchange column, and collecting the flow-through. Specifically, the sample may have a pH of 5.5-7.0 and a conductivity of 5-7 mS/cm.

According to the method of the present invention, a purified antibody comprising a significantly reduced amount of host cell protein (HCP) can be produced from a mixture comprising an antibody and at least one host cell protein (HCP) without having to use a protein-A column process. In the case in which an antibody is to be expressed in host cells such as animal cells and to be collected therefrom, there may exist, in addition to the desired protein, host cell protein (HCP), host cell DNA(HCD) and growth factors, as well as isomers (e.g., acidic isomers and basic isomers of the desired antibody). Thus, in order to make an antibody agent, a purification process that removes impurities to provide an antibody with high purity and high quality is required, and particularly, a purification process capable of effectively removing host cell protein is required. However, a protein-A chromatography column is an expensive resin, and thus an antibody purified using the same is considerably expensive. For this reason, the use of protein A chromatography in experiments or studies that use antibodies has been limited. Thus, technology capable of purifying antibodies without using protein A chromatography has been required. However, in order to develop a process capable of reducing protein A in an antibody so as to enable the antibody to be used as a pharmaceutical agent and to optimize this process, it is required to determine the kind of column used, the order of purification, and optimized conditions, and for this reason, it was difficult to actually develop this process. Accordingly, the present inventors have found that, when an antibody is purified by controlling the pH and conductivity of a culture supernatant of host cells that express the antibody and applying the controlled supernatant culture sequentially to cation-exchange chromatography, a multilayer filter and anion-exchange chromatography, the level of host cell protein in the antibody can be significantly reduced even by only a two-step chromatography process. Based on this finding, the present invention provides a method for purifying an antibody.

Step (a) in the method of the present invention is a first purification step of purifying a sample comprising the antibody to be purified and at least one host cell protein (HCP) by a cation-exchange column to remove the host cell protein from the sample. Specifically, step (a) is a step of loading a sample, which comprises an antibody and at least one host cell protein (HCP) and has a pH of 5.5-7.0 and a conductivity of 5-7 mS/cm, onto an equilibrated cation-exchange column, washing the cation-exchange column, and eluting the antibody, bound to the column, with elution buffer.

As used herein, the expression "sample which comprises an antibody and at least one host cell protein" means a culture supernatant of cells that produce the antibody, a lysate of the cells, or a sample partially purified therefrom, which comprises the desired antibody to be purified and host cell protein. As used herein, the term "partially purified" means a state in which other proteins are present in addition to the antibody to be purified, even after the purification process was performed.

Herein, the sample may be one controlled to have a pH of 5.5-7.0 and a conductivity of 5-7 mS/cm in order to effectively remove host cell protein therefrom according to the method of the present invention. If a sample having such a pH and conductivity is applied to cation-exchange chromatography, the protein to be purified can be easily adsorbed onto the cation-exchange column, while impurities such as host cell protein can be released by flow through during loading or can bind weakly or nonspecifically to the cation-exchange resin so as to be easily removed in a washing step.

As used herein, the term "conductivity" means the ability of an aqueous solution to pass electric current between two electrodes. In a solution, electric current flows by ion transport. Thus, if the amount of ions in an aqueous solution is increased, the solution will have increased ion conductivity. Because electric conductivity means the ability of ions in a solution to carry electric current, the conductivity of the solution can be changed by changing the ion concentration of the solution. For example, to obtain desired conductivity, the concentration of buffer and/or salt (e.g., sodium chloride, sodium acetate, or potassium chloride) in a solution can be changed. Preferably, desired conductivity can be obtained by changing the salt concentration of various buffers.

As used herein, the term "antibody" refers to a substance that is produced by stimulation of an antigen in the immune system and that binds specifically to a specific antigen to cause an antigen-antibody reaction in lymphocytes and blood. For the purpose of the present invention, the antibody is a protein to be purified with high purity and high quality and can be efficiently purified according to the method of the present invention.

Particularly, an antibody group purified by the method of the present invention is composed of antibodies obtained from the same group, but may include antibodies having a naturally occurring mutation, which can be present in trace amounts. As used herein, the term "antibody" is also meant to include an antibody group including one or more antibodies.

The antibody generally has a high isoelectric point compared to other proteins, and thus when a culture supernatant is adsorbed onto a cation-exchange resin column and eluted, the antibody can be primarily purified with a relatively high purity. As used herein, the term "isoelectric point (pI)" means the pH at which the average net charge of the protein molecule surface, that is, the potential of the electric double layer of the protein molecule, is 0. In other words, the term means the point at which the group of proteins is dissociated so that the numbers of cations and anions are equal, and thus the net charge of the protein is 0. An antibody that may be effectively purified by the method of the present invention may preferably have an isoelectric point of 6-11, and more preferably 7-10, but is not limited thereto. Antibodies that can be effectively purified by the method of the present invention while having the above-described isoelectric point include, but are not limited to, the antibody Bevacizumab that targets VEGF-A (vascular endothelial growth factor A), and the antibody Adalimumab that targets TNF-α, as well as all therapeutic antibodies that are generally used in the art while having the above-described isoelectric point. In an example of the present invention, it was shown that, when the inventive method comprising a two-step column process and a multilayer filtration step was used, HCP could be reduced to 1.0 ppm for Bevacizumab and 0.38 ppm for Adalimumab (Examples 3 and 4).

As used herein, the term "host cell protein (HCP)" means a protein different from the antibody, which is a protein derived from a source for antibody production, that is, host cells. In an antibody that may be used as a drug, HCP is preferably removed from the original antibody agent. As used herein, the expression "host cell protein that is removed" is meant to include all impurities excluding the antibody to be purified, including, in addition to host cell protein itself, the DNA and cell growth factors derived from host cells. Thus, when the host cell protein is removed, the purity of antibody can be increased significantly.

As used herein, the term "cation exchange chromatography" means chromatography utilizing a column packed with cation exchange resin. In step (a), impurities, particularly host cell protein, can be removed by performing cation exchange chromatography. The cation exchange resin is a synthetic resin that exchanges its cations with cations of an aqueous solution, and the antibody has high isoelectric point, and thus becomes cationic in a pH buffer having an isoelectric point lower than that of the antibody. Thus, according to the method of the present invention, the efficiency of antibody purification can be increased using the cation exchange resin capable of adsorbing the cationic antibody. Particularly, the efficiency of antibody purification can further be increased by loading a sample having a pH of 5.5-7.0 and a conductivity of 5-7 mS/cm into the cation exchange resin.

According to the present invention, when a sample comprising the antibody to be purified and host cell protein is loaded into the cation exchange resin, the antibody binds to the cation exchange resin, and impurities including host cell protein pass through the column (Flow-through chromatography) without binding or binding only weakly to the column. Thus, the antibody to be purified can be obtained by loading the sample into the cation exchange resin, treating the column with washing buffer to remove the host cell protein bound weakly to the column, and then treating the column with elution buffer.

The cation exchange resin that is used in the present invention may be one that is generally used in the art. Preferably, it may have a functional group such as carboxymethyl (CM), sulfoethyl (SE), sulfopropyl (SP), phosphate (P) or sulfonate (S), but is not limited thereto. More preferably, it may have carboxylate (COO—) or sulfonate ($SO_3$) as a functional group. As a cation exchange resin having a sulfonate group as a functional group, Fractogel™ EMD $SO_3$ may be used, but is not limited thereto.

A method of purifying an antibody using Fractogel™ EMD $SO_3$ as the cation exchange resin may preferably comprise the step of: (i) loading a sample comprising the antibody onto Fractogel™ EMD $SO_3$ column equilibrated with an equilibration buffer comprising 10-50 mM phosphate (pH 5.5-7.0); (ii) washing the column with a buffer comprising 20-40 mM sodium chloride and 10-50 mM phosphate (pH 6.0-7.0); and (iii) eluting the antibody with an elution buffer comprising 50-200 mM sodium chloride and 10-50 mM phosphate (pH 6.0-7.0).

The content of host cell protein (HCP) in the antibody eluate of step (a) may be lower than that in the loaded sample by 90-99.9%, preferably 95-99.5%.

In an example of the present invention, it was shown that the reduction rate of HCP was about 99.3% for the antibody Bevaczumab (Example 3) and about 98.8% for the antibody Adalimumab (Example 4).

Step (b) in the method of the present invention is a second purification step of removing host cell protein by passing the eluate of step (a) through a multilayer filter and collecting the filtrate.

The second purification step is performed in order to further increase the purity of the antibody by removing impurities including host cell protein, which were not removed in the first purification step. In this step, host cell protein can be more effectively removed using a filtration device capable of removing host cell protein by electrostatic charges and hydrophobic reactions according to a separation mechanism different from that of the cation exchange column of the first purification step.

This antibody eluate of step (a) that is injected into the multilayer filter includes the antibody eluate itself resulting from step (a) or a form obtained by processing the eluate. For example, the antibody eluate of step (a) that is used in step (b) of the present invention may be subjected to viral inactivation before it is passed through the multilayer filter.

Herein, the viral inactivation includes inactivating virus comprised in the eluate or removing virus from the eluate.

Methods for inactivating or removing the virus include, but are not limited to, heat inactivation, pH inactivation and chemical inactivation methods. Preferably, the pH inactivation method may be used. The pH inactivation method is a method of treating the eluate at a pH at which the virus in the eluate can be sufficiently inactivated. This pH inactivation method includes a low-pH viral inactivation method, which can be performed by titrating the antibody eluate of step (a) at a pH of 3.0-4.0, preferably 3.8, but is not limited thereto.

In addition, the antibody eluate of step (a) may be adjusted to a pH of 5.5-7.0, preferably 6.0, after the viral inactivation step, but before its passage through the multilayer filter, but is not limited thereto.

Herein, the pH of the antibody eluate can be adjusted using a buffer. The buffer that is used herein may preferably be Bis-Tris or phosphate buffer, and more preferably Bis-Tris buffer, but is not limited thereto.

In addition, it is preferable to adjust the pH and or conductivity of the antibody eluate of step (a) before passing the eluate through the multilayer filter. In this case, the antibody eluate can be adjusted to a pH of 5.5-7.0 and a conductivity of 1.2-10 mS/cm, preferably 1.3-5 mS/cm.

As used herein, the term "multilayer filter" means a filtration device comprising diatomaceous earth. This multilayer filter may be composed of a series of stacked filters having gradually decreasing pore sizes and may have a three-dimensional matrix structure such as a maze. Examples of the action mechanism of this multilayer filter include, but are not limited to, a mechanism in which the multilayer filter is cationic, and thus binds anionic substances such as DNA and host cell protein, thereby effectively removing host cell protein. The multilayer filter that is used in the present invention may be one that is generally used in the art. It may preferably be X0HC, A1HC (Millipore) or the like, and more preferably X0HC, but is not limited thereto.

The amount of host cell protein (HCP) in the antibody eluate obtained through this multilayer filtration process may preferably be 1,200-2,500 times smaller than that in the antibody eluate of step (a).

In an example of the present invention, it was shown that the content of HCP was reduced to 2.2 ppm (about 1/2,200) for the antibody Bevaczumab (Example 3) and 6.58 ppm (about 1/1400) for the antibody Adalimumab (Example 4).

Step (c) in the method of the present invention is a step of removing host cell protein using an anion exchange column. Specifically, step (c) is a third purification step of passing the filtrate of step (b) through an anion exchange column and collecting the flow-through.

As used herein, the term "anion exchange chromatography" means chromatography employing a column packed with anion exchange resin. In this step, impurities, particularly host cell protein, can be removed by performing anion exchange chromatography.

As used herein, the term "anion exchange resin" means a synthetic resin that exchanges its anions with the anions of an aqueous solution. The anion exchange column can adsorb a protein that becomes anionic above the isoelectric point. The antibody has a high isoelectric point, and thus when a neutral pH buffer is used, the antibody passes through the column without binding to the anion exchange resin. However, impurities including host cell protein have a low isoelectric point, and thus can be removed by adsorption onto the anion exchange resin. Accordingly, using this principle, the third purification step can be performed.

The anion exchange resin that is used in the present invention may be one that is generally used in the art. It may preferably be Q Sepharose, quaternary aminoethyl or quaternary amine (Q), and more preferably Q Fast Flow™, but is not limited thereto.

In the anion exchange chromatography utilizing Q Fast Flow™, Bis-Tris buffer or phosphate buffer may be used as equilibration buffer. In an example of the present invention, Q Fast Flow™ was used as anion exchange resin, and Bis-Tris buffer was used as equilibration buffer (Example 1-4).

As used herein, the expression "host cell protein that is removed" is meant to include all impurities excluding the antibody to be purified, including, in addition to host cell protein itself, the DNA and cell growth factors derived from host cells. Thus, when the host cell protein is removed, the antibody to be purified can be purified with high purity.

In addition, the anion exchange column is effective for the removal of not only host cell protein, but also endotoxin. Thus, it has an advantage in that it can remove endotoxin together with host cell protein in the final purification step, thereby purifying the desired antibody with high purity.

Through the antibody purification method comprising steps (a) to (c) of the present invention, that is, the two-step column process, an antibody from which impurities, particularly host cell protein, was efficiently removed, can be purified with high purity and high yield.

The content of host cell protein in the antibody after the final purification step may preferably be 0.001-10 ppm, and more preferably 0.01-5 ppm. In one example of the present invention, it was shown that the content of host cell protein was reduced to less than 5,000 ppm after the first purification step, less than 5 ppm after the second purification step, and less than 1.0 ppm after the third purification step (Example 3).

Particularly, it was found that the antibody Adalimumab could show an HCP content of 0.38 ppm even by only three steps (cation exchange column step, multilayer filter step, and anion exchange column step), suggesting that the method of the present invention has an excellent effect (Example 3). Thus, the method of the present invention shows an effect of purifying the antibody with a purity of 99.9% or higher, indicating that the method of the present invention can be advantageously used for antibody purification.

In addition, the method of the present invention can provide an antibody with a desired purity even by only the two-step column process (cation exchange column→multilayer filter→anion exchange column), but may comprise an additional purification step. Specifically, examples of the additional purification process that may be performed before, after or during the ion exchange chromatography process include fractionation on hydrophobic interaction chromatography (HIC), ethanol precipitation, ammonium sulfate precipitation, hydroxylapatite chromatography, gel electrophoresis, dialysis, and affinity chromatography (using, e.g., protein A, protein G, antibody-specific substrate, ligand or antigen as a capture reagent).

Mode for the Invention

Hereinafter, the present invention will be described in detail with reference to examples. It is to be understood, however, that these examples are for illustrative purposes and are not intended to limit the scope of the present invention.

Example 1: Bevacizumab Purification Method Using Two-Step Ion Exchange Column—Process A Example 1-1: Pretreatment Step Recombinant CHO cells expressing the Bevacizumab antibody were cultured to express the Bevacizumab antibody. Then, in order to adsorb the antibody onto a cation exchange column, 1M glycine HCl (pH 3.0) buffer was added to the culture supernatant to adjust the pH to 6.0 and the conductivity to 6.5 mS/cm.

Example 1-2: Cation Exchange Column Chromatography

In this example, Fractogel™ EMD $SO_3$ column was used as a cation exchange column, and cation exchange column chromatography was performed in the following manner.

For equilibration, the column was equilibrated with 20 mM phosphate buffer (pH 6.0), and the pretreated supernatant of Example 1 was loaded onto the column in an amount equal to or smaller than the adsorption capacity of $SO_3$. The loading amount was 30 g or less of protein per liter of resin, and the loading speed was 150 cm/hr.

After loading, the column was washed once with 20 mM phosphate buffer (pH 6.0), washed with 20 mM phosphate buffer (pH 6.5) comprising 30 mM sodium chloride, and then eluted with 20 mM phosphate buffer (pH 6.5) comprising 60 mM sodium chloride, thereby obtaining a primary eluate.

Example 1-3: Viral Inactivation and Equilibration

To the primary eluate obtained in Example 1-2, 1M glycine-HCl (pH 3.0) buffer was added, and then the solution was subjected to viral inactivation at a pH of 3.8 for 1 hour. After completion of viral inactivation, the solution was filtered through a 0.2 μm filter, and then the pH of the sample was adjusted to 6.0 by adding 1M Tris-HCl (pH 9.0) buffer thereto. The sample after viral inactivation was substituted with 20 mM Bis-Tris (pH 6.0) buffer.

Example 1-4: Anion Exchange Column Chromatography

An anion exchange column adsorbs a protein that becomes anionic above its isoelectric point. Thus, when a neutral pH buffer is used, an antibody having an isoelectric point of 7 or higher (8.3 for Bevaczumab) will flow through the column without binding to the anion exchange resin. Accordingly, to determine an anion exchange resin and buffer conditions suitable for use in the purification process of the present invention, the following experiment was performed.

Specifically, in this Example, quaternary amine series Q Sepharose™ Fast flow that is frequently used in production scale was used as the anion exchange resin to perform purification.

First, the sample for loading onto the anion exchange resin was adjusted to a pH of 6.0 and a conductivity of 1.4 mS/cm by substitution with 20 mM Bis-Tris (pH 6.0) equilibration buffer, after cation exchange column chromatography of the culture supernatant, viral inactivation, and first ultrafiltration were performed as described in the above Example.

The loading amount was 30 g or less of protein per liter of resin, and the loading and elution speed was 150 cm/hr. When the absorbance at 280 nm increased, the column flow-through fraction was collected. The column was regenerated with 1M NaCl, and then equilibrated with equilibration buffer.

Process A as described above is summarized in Table 1 below.

TABLE 1

| Process A | Content |
| --- | --- |
| Step 1 (pretreatment step) | Adjusting the pH and conductivity of a mixture of antibody and HCP |
| Step 2 (cation exchange column) | i) loading amount = 30 g protein/1 L resin/cycle, V = 150 cm/hr, equilibrated with 20 mM phosphate buffer. ii) After loading of Bevaczumab, the column was washed once with equilibration buffer and eluted with elution buffer comprising sodium chloride, thereby obtaining a first eluate |
| Step 3 (viral inactivation) | i) Inactivation at low pH for 1 hour. ii) After completion of inactivation, adjustment to neutral pH, followed by ultrafiltration. |
| Step 4 (anion exchange column) | Loading amount ≤30 g protein/L resin/cycle, V = 150 cm/hr, equilibrated with Bis-Tris equilibration buffer, followed by collection of flow-through fraction. |

Example 2: Bevacizumab Purification Method Using Multilayer Filter—Process B The pretreatment step, cation exchange column chromatography, and viral inactivation/equilibration step in process B were as described in Examples 1-1 to 1-3.

Example 2-1: Multilayer Filtration (Depth Filtering)

A multilayer filter can reduce the amounts of host cell DNA (HCD), host cell protein (HCP) and the like by its electrostatic properties. Accordingly, a X0HC-type multilayer filter was prepared and equilibrated with triple-distilled water and 20 mM Bis-Tris (pH 6.0) buffer. Then, the virus-inactivated sample was substituted with 20 mM Bis-Tris (pH 6.0) buffer as described in Example 1-4, and then filtered through the multilayer filter at and subjected to anion exchange column chromatography as described in Example 2-2 below.

Example 2-2: Anion Exchange Column Chromatography

Anion exchange column chromatography is as described in Example 1-4 above. However, the sample was loaded into the anion column chromatography column, after cation exchange column chromatography of the culture supernatant, viral inactivation, first ultrafiltration, and filtration through the multilayer filter were performed as described above.

Herein, the loading amount was 30 g or less per liter of resin, and the loading and elution speed was 150 cm/hr. When the absorbance at 280 nm increased, the column flow-through fraction was collected. The column was regenerated with 1M NaCl, and then equilibrated with equilibration buffer.

Process B as described above is summarized in Table 2 below.

TABLE 2

| Process B | Content |
| --- | --- |
| Step 1 (pretreatment step) | Adjusting the pH and conductivity of a mixture of antibody and HCP |
| Step 2 (cation exchange column) | i) loading amount = 30 g protein/1 L resin/cycle, V = 150 cm/hr, equilibrated with 20 mM phosphate buffer. ii) After loading of Bevaczumab, the column was washed once with equilibration buffer and eluted with elution buffer comprising sodium chloride, thereby obtaining a first eluate |
| Step 3 (viral inactivation) | i) Inactivation at low pH for 1 hour. ii) After completion of inactivation, adjustment to neutral pH, followed by ultrafiltration. |
| Step 4 (Multilayer filter) | i) X0HC-type multiple filter was prepared and equilibrated with Bis-Tris buffer. ii) sample was filtrated at a flow rate of 100 LMH, and the filtrate was collected. |
| Step 5 (anion exchange column) | Loading amount ≤30 g protein/L resin/cycle, V = 150 cm/hr, equilibrated with Bis-Tris equilibration buffer, followed by collection of flow-through fraction. |

Example 3: Detection and Comparison of Host Cell Protein (HCP)

To measure the concentration of host cell protein (HCP) in the antibody sample obtained in the above-described Examples, the HCP ELISA method was used.

Specifically, according to enzyme-linked immunosorbent assay (ELISA), the HCP antigen comprising the antibody sample was attached to immobilized primary antibody. Then, nonspecific regions were blocked with casein. Then, the sample was incubated while the antigen molecule was captured by the primary antibody. Then, HRP (horseradish peroxidase)-conjugated secondary antibody was added thereto and fixed to the antigen (CHO host cell protein). TMB (3,3',5,5'-tetramethylbenzidine) was added to the sample to develop a color, and then sulfuric acid was added to stop the reaction. The color of the reaction solution changed to yellow. The color intensity was directly proportional to the amount of antigen bound to the well.

The content of host cell protein was measured by HCP ELISA as described above, and the data were expressed in ng HCP/mg (ppm) (Table 3).

In the case of process A, a HCP content of 671,922.5 ppm before loading onto the cation exchange column was reduced to 4,791.2 ppm (about 1/140) after purification by the cation exchange column. Then, the HCP content was reduced to 61.4 ppm (about 1/75) after purification by the anion exchange column.

In the case of process B, the content of HCP was reduced to about 1/670,000. Specifically, in the cation column exchange chromatography step, the content of HCP was reduced to 1/140, and in the multilayer filter step following the cation column exchange chromatography step, the content of HCP was reduced to 1/2,100 compared to that of the primary eluate. In the final anion exchange column chromatography step, the content of HCP was reduced to about 1/2.

It could be seen that, when compared to process A that reduced the content of HCP to about 1/11,000, process B more greatly reduced the content of HCP because the multilayer filter step was performed.

TABLE 3

|  | HCP content (ppm) in process A | HCP content (ppm) in process B |
|---|---|---|
| Culture | 671992.5 | 671992.5 |
| Cation exchange column | 4791.2 | 4791.2 |
| Multilayer filter | — | 2.2 |
| Anion exchange column | 61.4 | 1.0 |

Example 4: Purification of Adalimumab

In order to purify the Adalimumab antibody from a mixture of Adalimumab and host cell protein (HCP), a buffer was added to a cell-free culture supernatant to adjust the pH and conductivity of the supernatant, and the supernatant was filtered to prepare a sample for loading into a cation exchange column. Then, the sample was subjected to the multilayer filter and anion exchange column chromatography steps in the same manner as described in Example 2. A sample was collected from the Adalimumab purification process, and the content of HCP in the collected sample was analyzed. The results of the analysis are shown in Table 4 below. When the inventive process comprising the multilayer filter step was used to purify Adalimumab, the content of HCP could be reduced to about 1/2,000,000.

TABLE 4

|  | HCP (ppm) |
|---|---|
| Culture | 747204.8 |
| Cation exchange column | 9466.1 |
| Multilayer filter | 6.58 |
| Anion exchange column | 0.38 |

While the present invention has been described with reference to the particular illustrative embodiments, those skilled in the art to which the present invention pertains can understand that the present invention may be embodied in other specific forms without departing from the technical spirit or essential characteristics of the present invention. Therefore, the embodiments described above are considered to be illustrative in all respects and not restrictive. Furthermore, it should be understood that all modifications or variations derived from the meanings and scope of the present invention and equivalents thereof are included in the scope of the appended claims.

The invention claimed is:

1. A method for purifying an antibody, the method comprising:

(a) loading a sample, which comprises the antibody and at least one host cell protein (HCP) and has a pH of 5.5-7.0 and a conductivity of 5-7 mS/cm, into an equilibrated cation-exchange column, washing the cation-exchange column, and then eluting the antibody bound to the column with elution buffer;

(b) passing the eluate of step (a) through a multilayer filter, and collecting the filtrate; and (c) passing the filtrate of step (b) through an anion-exchange column, and collecting the flow-through.

2. The method according to claim 1, wherein the antibody has an isoelectric point of 7-10.

3. The method according to claim 1, wherein the antibody is Bevacizumab or Adalimumab.

4. The method according to claim 1, wherein the content of host cell protein (HCP) in the antibody eluate of step (a) is 95-99.5% lower than that in the loaded sample.

5. The method according to claim 1, wherein the cation exchange column has a functional group selected from the group consisting of carboxymethyl (CM), sulfoethyl (SE), sulfopropyl (SP), phosphate (P) and sulfonate (S).

6. The method according to claim 5, wherein the cation exchange column having sulfonate as a functional group comprises a cross-linked polymethacrylate resin.

7. The method according to claim 6, wherein step (a) comprises:

(i) loading the sample comprising the antibody onto the cation exchange column equilibrated with an equilibration buffer comprising 10-50 mM phosphate (pH 5.5-7.0);

(ii) washing the cation exchange column with a buffer comprising 20-40 mM sodium chloride and 10-50 mM phosphate (pH 6.0-7.0); and (iii) eluting the antibody with an elution buffer comprising 50-200 mM sodium chloride and 10-50 mM phosphate (pH 6.0-7.0).

8. The method according to claim 1, wherein the multilayer filter has a product water conductivity of 8.66-10.5 $\mu$S/cm or 19.34-53.2 $\mu$S/cm post autoclave and pure water flush of 10 liters per ft$^2$ (100 L/m$^2$) of surface area of the multilayer filter.

9. The method according to claim 1, wherein the antibody eluate of step (b) is subjected to viral inactivation before it is passed through the multilayer filter.

10. The method according to claim 1, wherein the antibody eluate of step (b) is adjusted to a pH of 5.5-7.0 before it is passed through the multilayer filter.

11. The method according to claim 1, wherein the content of host cell protein (HCP) in the filtrate of step (b) is 1,200-2,500 times lower than that in the antibody eluate of step (a).

12. The method according to claim 1, wherein the anion exchange column in step (c) has a functional group of a quartenary amine and further comprises a cross-linked agarose base matrix.

13. The method according to claim 1, wherein the content of host cell protein (HCP) in the protein purified by the method is 0.001-10 ppm.

14. The method according to claim 1, wherein the method comprises no additional column chromatography step.

* * * * *